United States Patent
Al-Oboudi (10) Patent No.: US 7,547,290 B1
(45) Date of Patent: Jun. 16, 2009

(54) ORTHOTIC DEVICE

(76) Inventor: Waleed Al-Oboudi, 4806 Via El Sereno, Torrance, CA (US) 90505

( * ) Notice: Subject to any disclaimer, the term of this patent is extended or adjusted under 35 U.S.C. 154(b) by 216 days.

(21) Appl. No.: 11/158,284

(22) Filed: Jun. 20, 2005

Related U.S. Application Data (60) Provisional application No. 60/580,928, filed on Jun. 18, 2004.

(51) Int. Cl.
*A61F 5/00* (2006.01)

(52) U.S. Cl. .............. 602/21; 602/5; 602/16; 602/20

(58) Field of Classification Search ............ 602/4, 602/20–22, 5, 16, 60, 61, 63; 128/877–881, 128/5; 482/46; D24/190
See application file for complete search history.

(56) References Cited

U.S. PATENT DOCUMENTS

| | | | | |
|---|---|---|---|---|
| 1,267,142 | A | * | 5/1918 | Stowers et al. .............. 602/4 |
| 1,708,757 | A | * | 4/1929 | Freileweh ................... 602/20 |
| 5,285,773 | A | | 2/1994 | Bonutti et al. |
| 5,503,619 | A | | 4/1996 | Bonutti |
| 6,113,562 | A | * | 9/2000 | Bonutti et al. ............... 602/20 |
| 6,599,263 | B1 | | 7/2003 | Bonutti et al. |
| 6,692,453 | B2 | | 2/2004 | Wolfe |
| 6,949,077 | B2 | * | 9/2005 | Froom ....................... 602/21 |
| 7,175,603 | B2 | * | 2/2007 | Fritsch et al. ............... 602/20 |
| 2005/0145255 | A1 | * | 7/2005 | Mengato ..................... 128/878 |

OTHER PUBLICATIONS

AliMed® Turnbuckle Functional Position Splint, 2006 AliMed® inc product catalog.
AliMed® Ball Splint, 2006 AliMed® inc product catalog.
AliMed® Deluxe Resting Pan Mitt Splint, 2006 AliMed® inc product catalog.
AliMed® Hemi Shoulder Sling, 2006 AliMed® inc product catalog.
GivMohr Sling, 2006 AliMed® inc product catalog.

* cited by examiner

*Primary Examiner*—Kim M Lewis
(74) *Attorney, Agent, or Firm*—Knobbe, Martens, Olson & Bear LLP (57) ABSTRACT

An orthotic device and method for reducing muscle hypertonicity and contractures in patients with neurological disorders are provided. The device includes a hand support that is configured to receive and position a patient's hand in a manner such that the arches and fingers of the hand are extended and the finger knuckles do not bend toward the palm of the hand. The device also includes a forearm support which is pivotably connected to the hand support. The patient's hand is pivoted upwardly with the fingers extended which facilitates elongating the flexor tendons and muscles. In certain implementations, the device also includes an elbow support that is pivotably connected to the forearm support. The device and method are effective in spreading the metacarpals with finger and thumb extensions.

10 Claims, 10 Drawing Sheets

ORTHOTIC DEVICE

RELATED APPLICATIONS

This application claims the benefit of U.S. Provisional Application Ser. No. 60/580,928, filed Jun. 18, 2004, which is hereby incorporated by reference in its entirety.

BACKGROUND OF THE INVENTION

1. Field of the Invention

This invention relates generally to orthotic devices, and more particularly, to an orthotic device for use in rehabilitating individuals suffering from muscle spasticity, hypertonicity, and contractures which may be caused by stroke or brain injury.

2. Description of the Related Art

Patients with neurological disorders often suffer from muscle spasticity, hypertonicity and contractures which are usually caused by damages to the systems that control voluntary movements. Spasticity and hypertonicity are demonstrated when muscles receive improper nerve signals causing them to contract and become shortened. Improper control of brain signals is often due to damage within the brain caused by stroke, brain injury, or other traumas.

Contracture is one of the most detrimental consequences of spasticity or hypertonicity. Contractures are generally due to shortening of muscle fibers and other soft tissues and structural changes. When a muscle is not regularly put through its full range of movement, it can shorten and result in an abnormal condition including abnormal joint posture. This makes stretching the muscle difficult and may set up a vicious cycle of even more shortening and decreased stretch. The end result of untreated contracture is a long-term, often painful, abnormal posture, such as over-flexion of the hand or inversion of the foot.

One primary type of treatment for muscle spasticity, hypertonicity and contractures is regular stretching exercises including lengthening of flexors prescribed by a physical and occupational therapist. Early on in contracture development, range of motion exercises can help prevent permanent tendon shortening. Treatments for the upper extremities typically also include using a splint to position the patient's hand and wrist in a manner so as to keep them in a position that maintains range. The splint usually has a hand support contoured in the shape of the patient's hand in which the fingers are partially flexed and the wrist is extended. The hand support typically includes an interior surface or padding that directly contacts substantially the entire interior side of the hand, including the arch region. As such, the hand may be in a power position to flex on an object, which in turn can trigger more finger and thumb flexion. Thus, the occurrence of contractures may actually increase when the patient wears most conventional splints intended to reduce and manage the contractures.

In view of the foregoing, there is a need for an improved orthotic device and method for treating patients with muscle spasticity, hypertonicity and contractures. To this end, there is a particular need for an orthotic device and approach of treatment that reduces the occurrence of muscle over-activity while at the same time reverses muscle and tendon contractures.

SUMMARY OF THE INVENTION

In one aspect, the preferred embodiments of the present invention provide an orthotic device for reducing contracture and hypertonicity in patients with neurological disorders. The device includes a hand support, a forearm support, and attachment member that secures the device to the patient's forearm and hand. In one embodiment, the hand support is configured to receive and position a patient's hand in a manner such that the fingers of the hand are extended and the finger knuckles do not bend toward the palm of the hand. Preferably, the forearm support is pivotably connected to the hand support by a ratchet joint or other devices. The forearm support is configured to receive at least a portion of the patient's forearm. In one embodiment, the hand support has a substantially planar interior surface wherein the interior surface comprises the palm rest portion and a fingers rest portion. In another embodiment, the hand support comprises a palm rest portion and a thumb rest portion. Preferably, the thumb rest portion is pivotable relative to the palm portion rest such that the angle therebetween can be adjusted. In yet another embodiment, the hand support has a plurality of padding wherein the padding located in areas where the digit fingers of the patient's hand is to be positioned.

In another aspect, the preferred embodiments of the present invention provide an orthotic device having a hand support that includes a palm rest portion. Preferably, the palm rest portion has a central portion and a peripheral portion surrounding the central portion. Preferably, the central portion is not substantially higher than the peripheral portion so as to cause the palm to receive force substantially from the peripheral portion. In one embodiment, the central portion is substantially below the peripheral portion so that the palm of the patient's hand receives force substantially entirely from the peripheral portion. In another embodiment, the hand portion further comprises a fingertip portion. The fingertip portion is preferably at substantially the same level as the peripheral portion of the palm rest portion so as to allow extensions of the patient's fingers without bending the finger knuckles.

In yet another aspect, the preferred embodiments of the present invention provide a method of reducing muscle hypertonicity and contractures in patients with neurological disorders. The method comprises positioning the patient's hand in a hand support structure in a manner such that the arch of the hand is extended and the finger knuckles do not bend toward the palm of the hand. The method further comprises pivoting the patient's hand upwardly relatively to the wrist so as to elongate the patient's flexor tendon and muscles. In one embodiment, the method also includes securing the patient's forearm in a forearm support that is pivotably connected to the hand support structure. In another embodiment, the method also includes securing the patient's elbow in an elbow support that is pivotably connected to the forearm support.

DETAILED DESCRIPTION OF PREFERRED EMBODIMENTS

Figure 1:
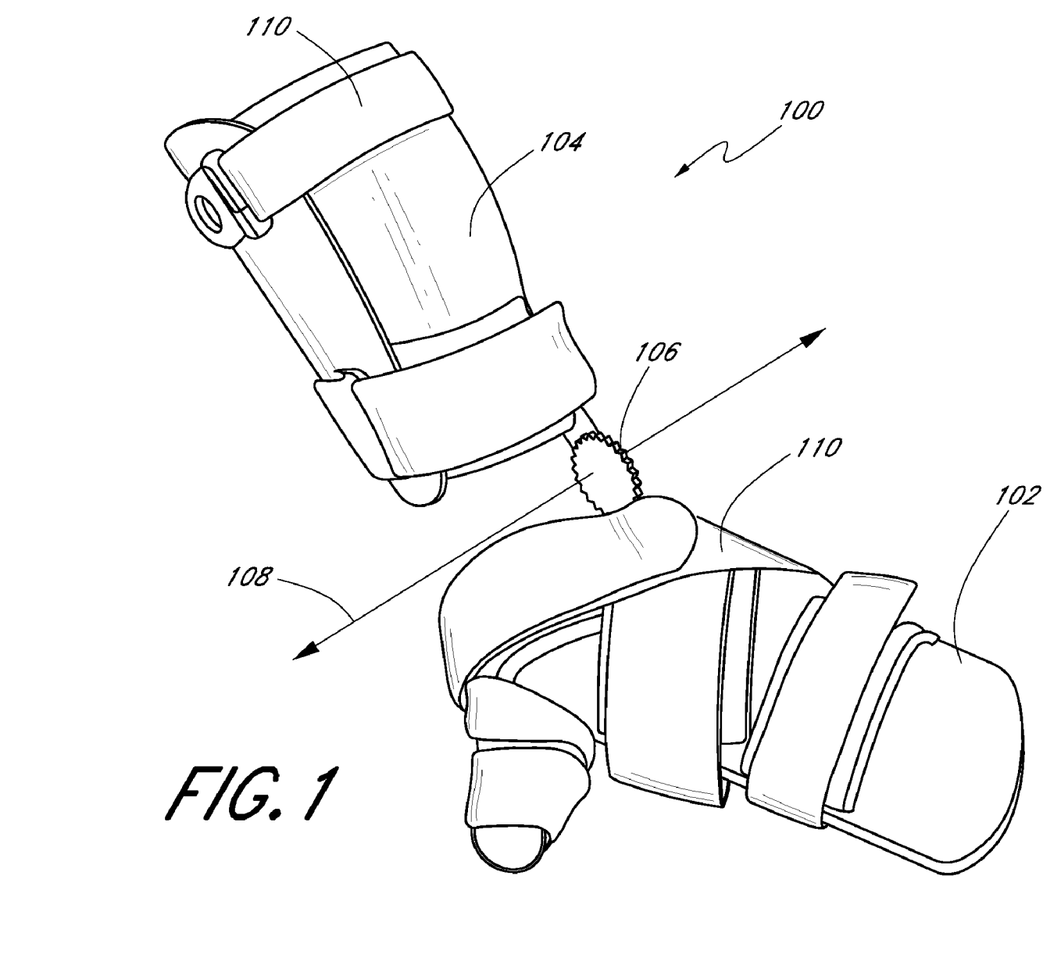
FIG. 1 is a perspective view of an orthotic device of one embodiment of the present invention.

FIG. 1 illustrates an orthotic device 100 of one preferred embodiment of the present invention. As shown in FIG. 1, the device 100 generally includes a hand support 102 and a forearm support 104 which are movably interconnected by a joint 106. Preferably, the hand support 102 and forearm support 104 are pivotable about a central axis 108 defined by the joint 106. In one embodiment, the joint 106 is a ratchet joint known in the art. The ratchet joint can be locked in a plurality of different positions so that the hand support 102 and forearm support 104 can be affixed at various angles relative to each other. In one embodiment, the angle between the hand support 102 and forearm support 104 can be set at about 180 degrees, 150 degrees, 130 degrees, 100 degrees, and 90 degrees. Additionally, the hand support 102 and forearm support 104 can be applied and secured to a patient's hand and forearm respectively by straps 110 or other attachment devices. As will be described in greater detail below, the device 100 is configured to position the patient's hand and wrist in a manner so as to lengthen hypertonic muscles and reverse contractor of the flexors.

Figure 2:
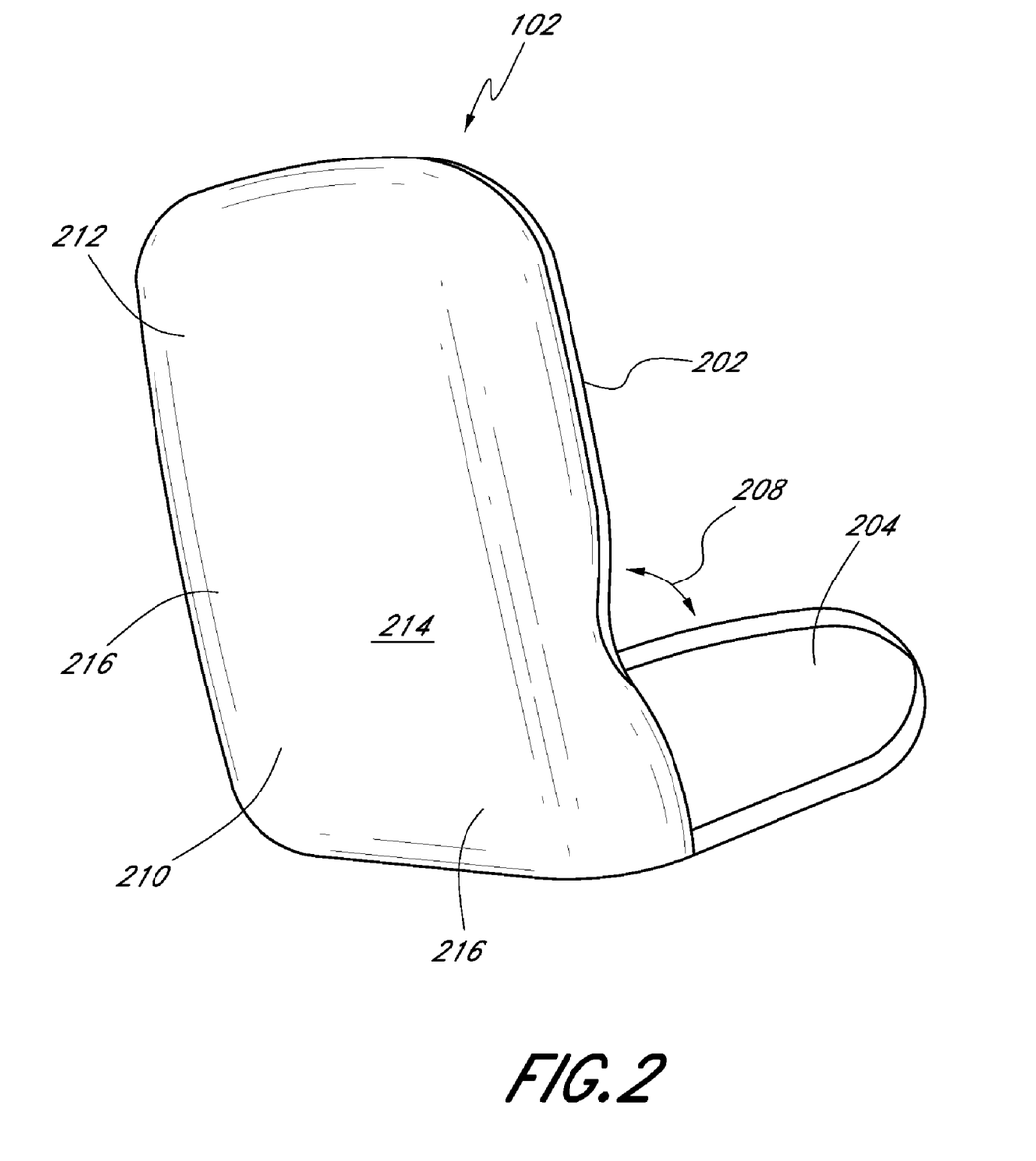
FIG. 2 is a detailed view of the hand support of the orthotic device of FIG. 1.

FIG. 2 further illustrates the hand support 102 of the orthotic device 100. For illustration purposes, the hand support 102 is shown without the straps in this figure. As shown, the hand support 102 is configured in the general shape of a human hand. The hand support 102 can be made of a variety of different materials including rigid thermoplastic materials. Preferably, the hand support 102 has a main support portion 202 and a thumb support portion 204. The thumb support portion 204 is configured to receive the thumb and preferably extends laterally from the main support portion 202. In one implementation, the thumb support portion 204 is pivotable relative to the main support portion 202 such that the angle 208 between them can be adjusted.

In a preferred embodiment, the main support portion 202 has a palm rest portion 210 and a digit fingers rest portion 212. The palm rest portion 210 includes a central portion 214 and a peripheral portion 216 which surrounds the central portion 214. Preferably, the interior surface of the palm rest portion 210 is not substantially higher than the interior surface of peripheral portion 216 so that when the patient's hand is positioned in the hand support 102, the palm receives force substantially entirely from the peripheral portion of the hand support. Moreover, the digit fingers rest portion 212 is preferably at the same level as the palm rest portion 210 so that the patient's fingers are extended without bending the knuckles.

In yet another preferred embodiment, the main support section 202 has a generally planar interior surface so as to allow full extension of the arches, metacarpal and fingers of the hand. However, it will be understood that the hand support 102 can be designed in any configuration that would allow the patient's hand to be positioned in a manner such that the hand lies relatively flat with the arch spread and the fingers extended and the finger knuckles do not bend toward the palm.

Figure 3A:
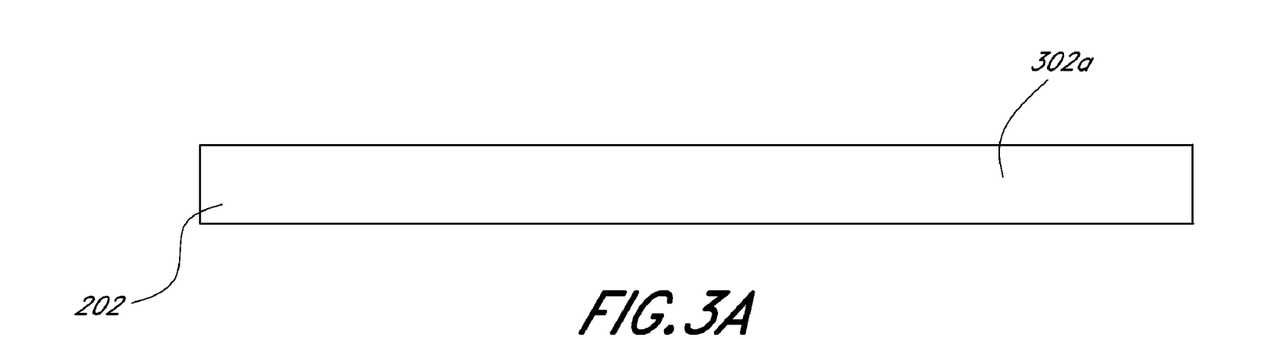
FIGS. 3A-3C are schematic illustrates of the cross-section of the hand support of certain preferred embodiments.
Figure 3B:
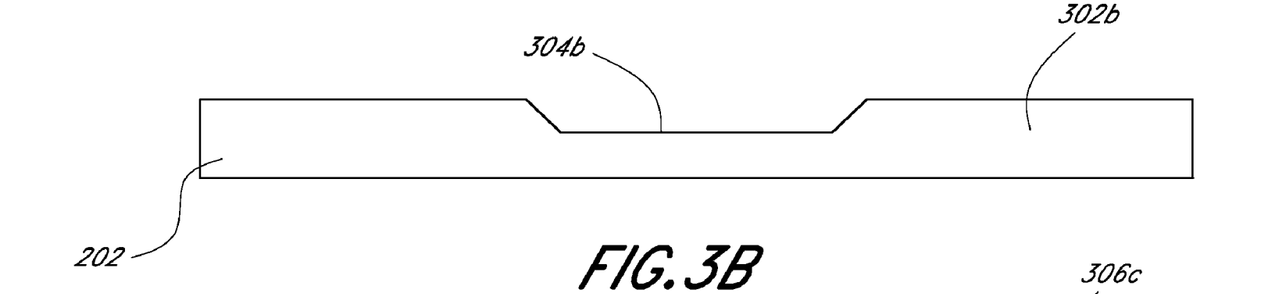
Figure 3C:
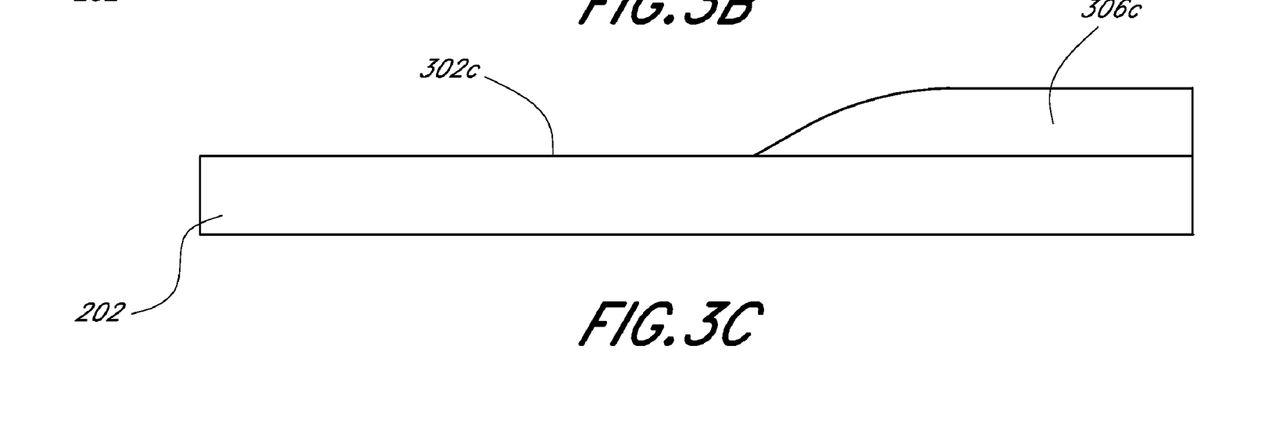

FIGS. 3A-3C schematically illustrate the general cross-sectional profile of the main support portions of certain preferred implementations of the device. In the embodiment shown in FIG. 3A, the main support portion 202 has a generally planar interior surface 302a configured to receive the patient's palm and digit fingers in a manner such that the hand lies flat against the interior surface of the hand support when the device is applied to the hand. In the embodiment shown in FIG. 3B, the interior surface 302b of the main support portion 202 is contoured in a manner such that the central arch region 304b of the patient's hand does not contact the interior surface 302b of the hand support when the device is applied to the hand. In this implementation, the interior surface is concaved at the location where the central arch region of the hand is to be positioned so as to avoid applying pressure to the arch region and flexor tendon therein when the hand is pressed against the interior surface. In the embodiment shown in FIG. 3C, one or more padding 306c is positioned on the inner surface 302c of the main support portion 202 at locations other than where the central arch region is to be positioned. In one embodiment, padding is placed at locations on the interior surface 302c which the patient's digit fingers are to be positioned so as to increase finger lift which allows for a fully extended position of the flexor tendon and muscles when excessive curling or flexion pattern is present. By avoiding contact with the central arch region of the hand and allowing the fingers to fully extend, the device 100 significantly reduces flexor spasticity or hypertonicity typically triggered by contacting or imparting pressure to the arch region and flexor tendon therein. As such, the orthotic device 100 is advantageously configured to elongate the flexor muscle while reducing muscle and tendon contracture, which provides a more effective therapeutic treatment for the patient than the known prior art orthotic devices and treatment systems.

Figure 4:
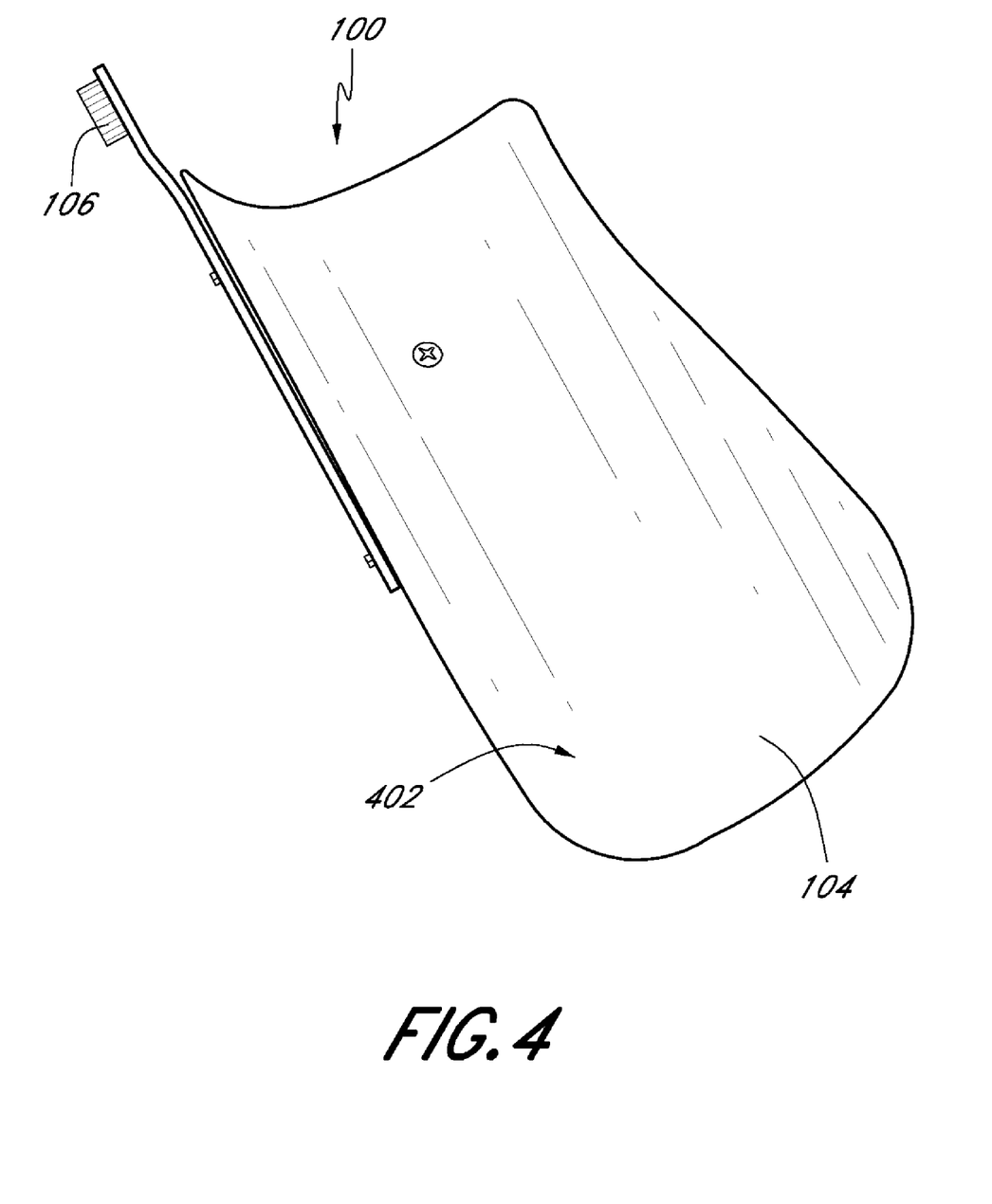
FIG. 4 is a detailed view of the forearm support of the orthotic device of FIG. 1.

FIG. 4 illustrates a detailed view of the forearm support 104 of the orthotic device 100. As shown in FIG. 3, the forearm support 104 is formed of a rigid, elongate thermoplastic article having a curved inner surface 402 contoured to receive and support the patient's forearm when the patient's hand is positioned in the hand support 102. The forearm support 104 is pivotably connected to the hand support by a ratchet joint. The forearm support 104 operates in conjunction with the hand support to maintain the patient's wrist and hand in a certain fixed angle.

Figure 5A:
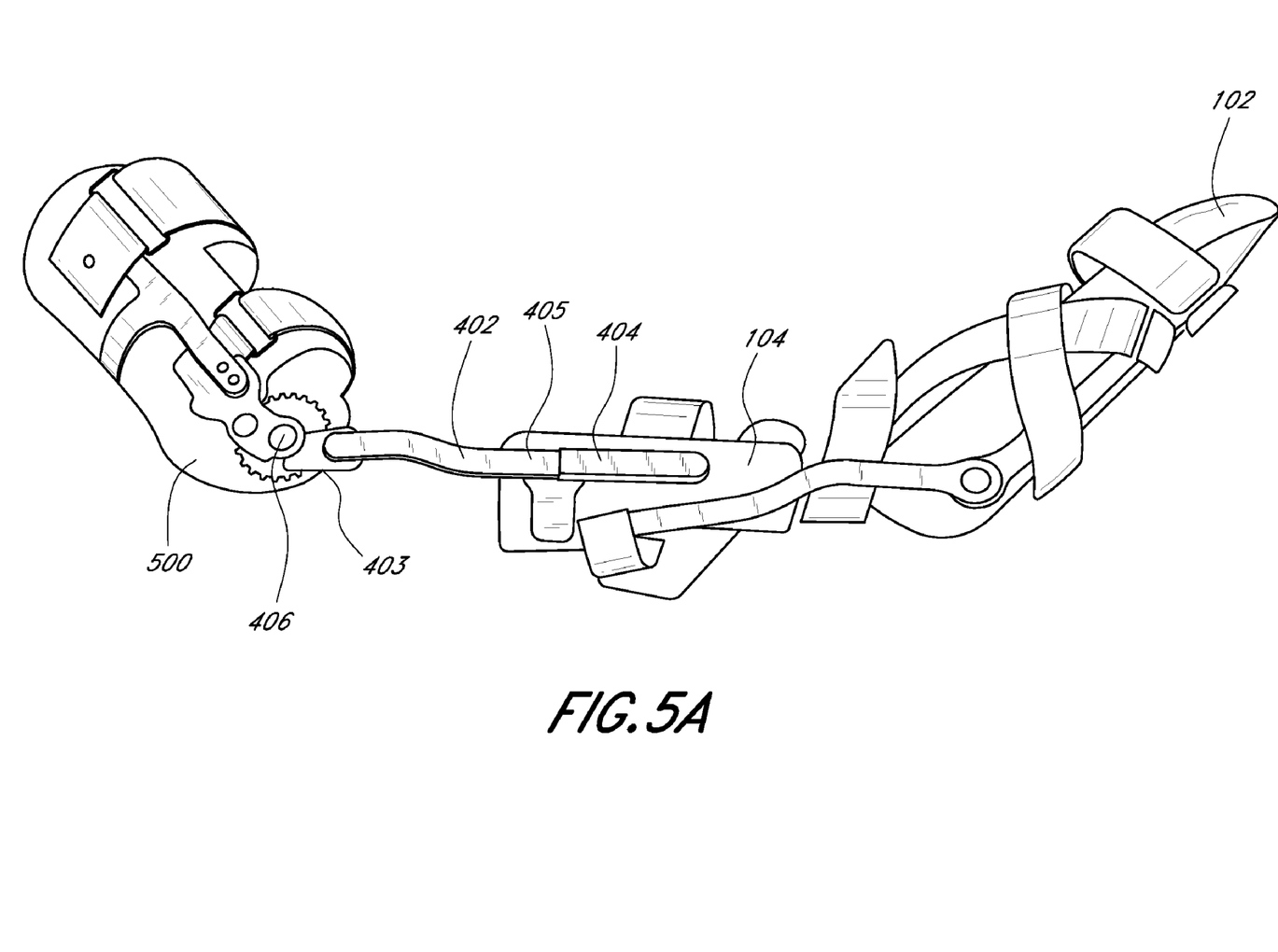
FIGS. 5A-5D illustrate an orthotic device of another embodiment of the present invention, including an elbow support.
Figure 5B:
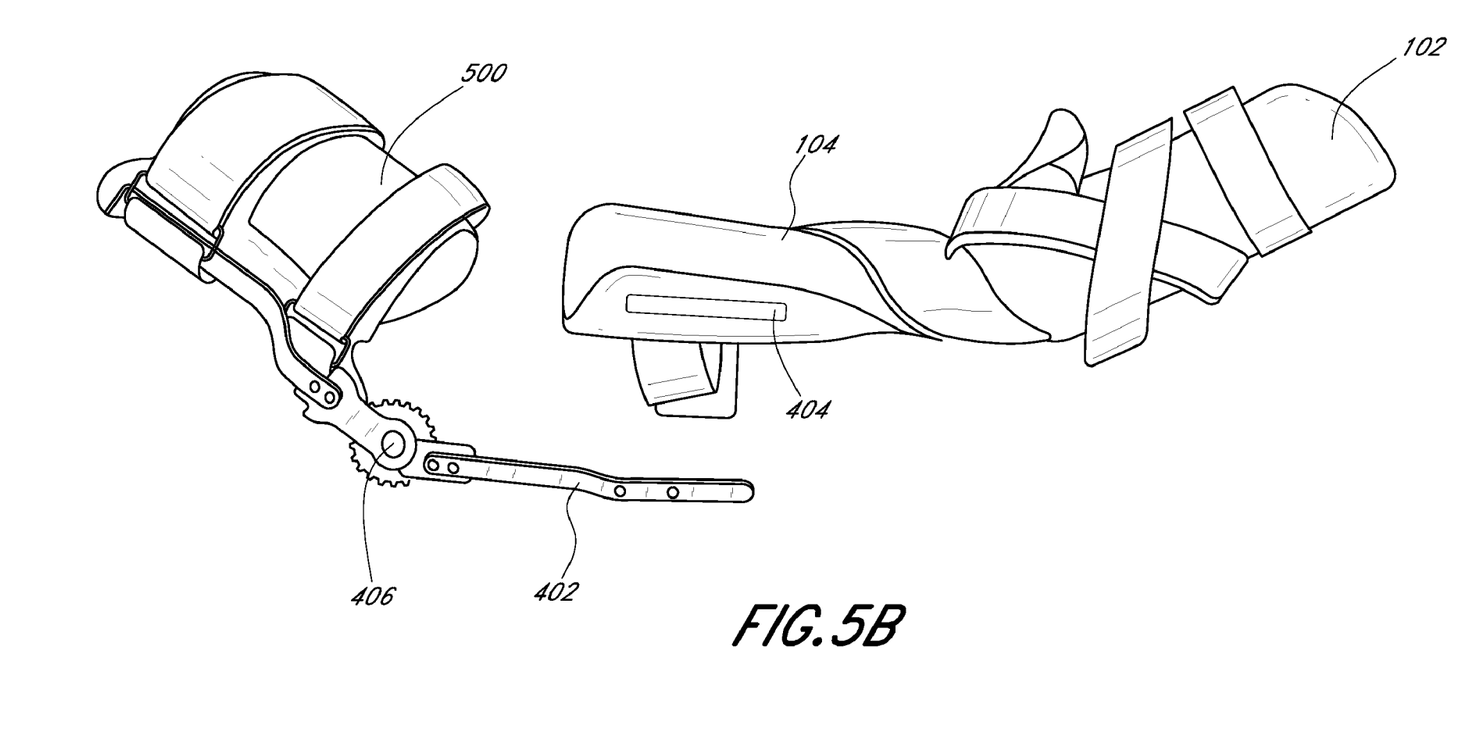
Figure 5C:
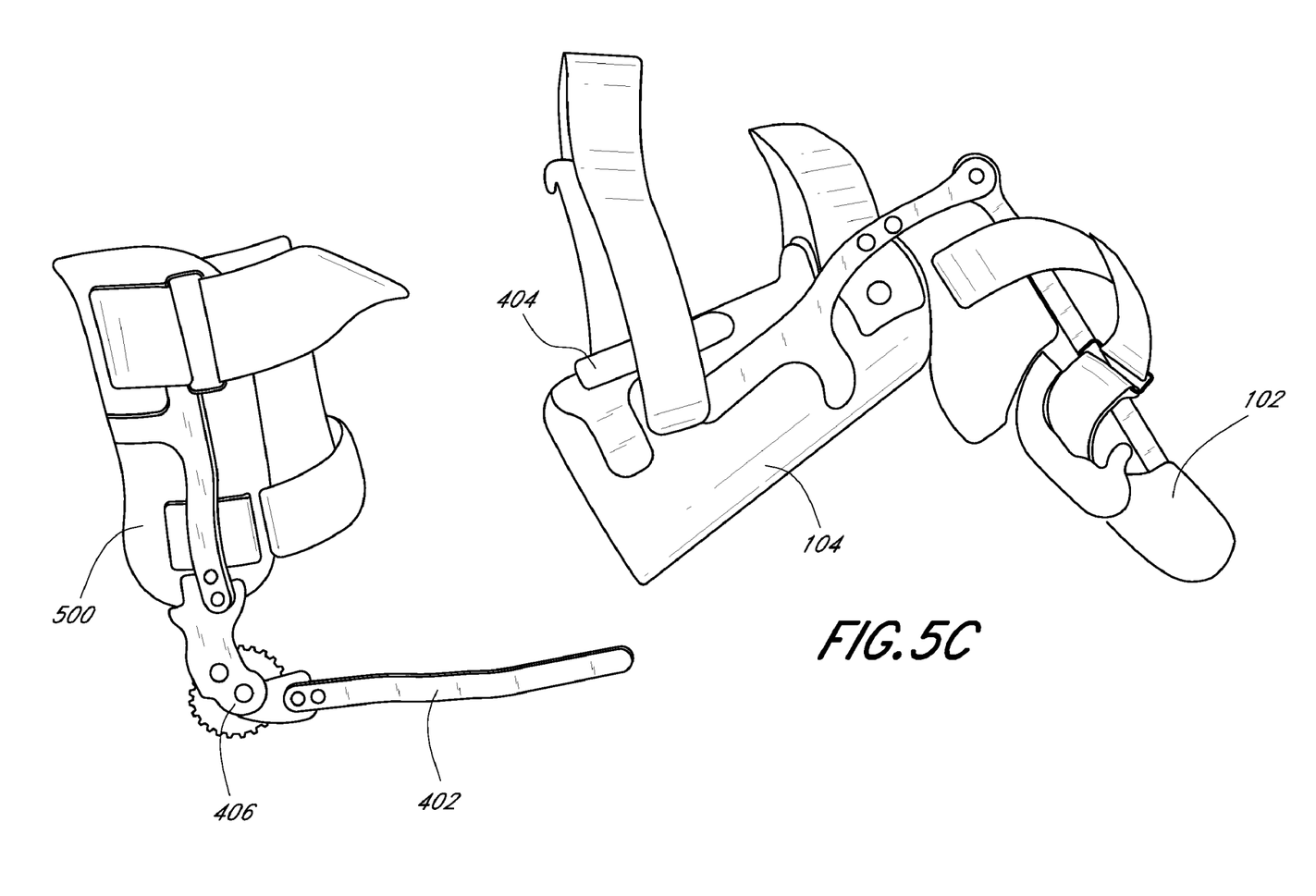
Figure 5D:
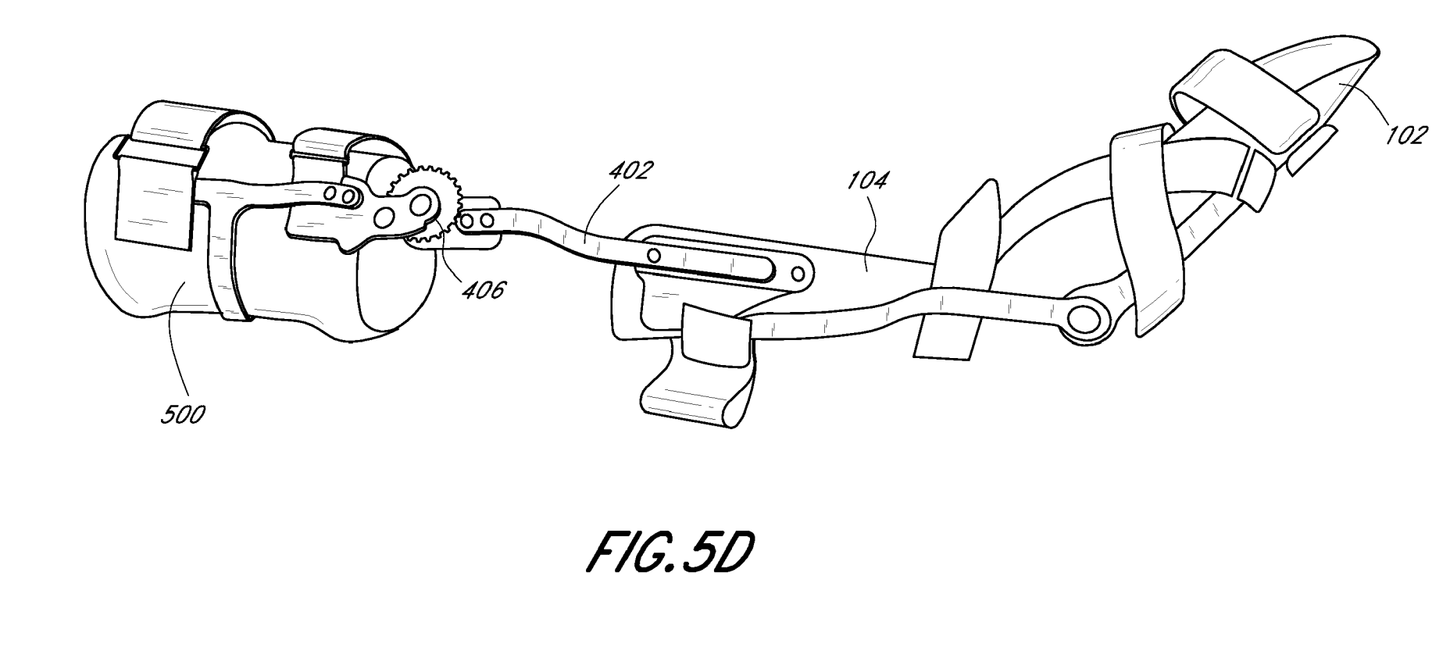

In certain embodiments, as shown in FIGS. 5A-D, the device 100 further includes an elbow support 500 that is configured to receive and support the elbow of the patient. As shown in FIG. 5A, the elbow support 500 is pivotably connected to and interlocks with the forearm support 104 of the device 100 via an interconnect member 402. A first end 403 of the interconnect member 402 is configured to pivotably attach to the elbow support 400 at a joint 406. A second end 405 of the interconnect member 402 is configured to slidably engage with a channel 404 attached to the forearm support 104 of the device 100. The distance between the elbow support 400 and the forearm support 104 can thus be adjusted by sliding the interconnect member 402 in and out of the channel 404. This accommodates changes in the distance between the elbow support 400 and the forearm support 104 as the patient's forearm is raised or lowered relative to the elbow. In certain other embodiments, the device 100 also includes a shoulder support that is adapted to reduce the occurrence of traction of the shoulder. Instead of anchoring the shoulder support on the patient's back and neck area, the shoulder support of the preferred embodiment is anchored to the waist area of the patient.

Figure 6:
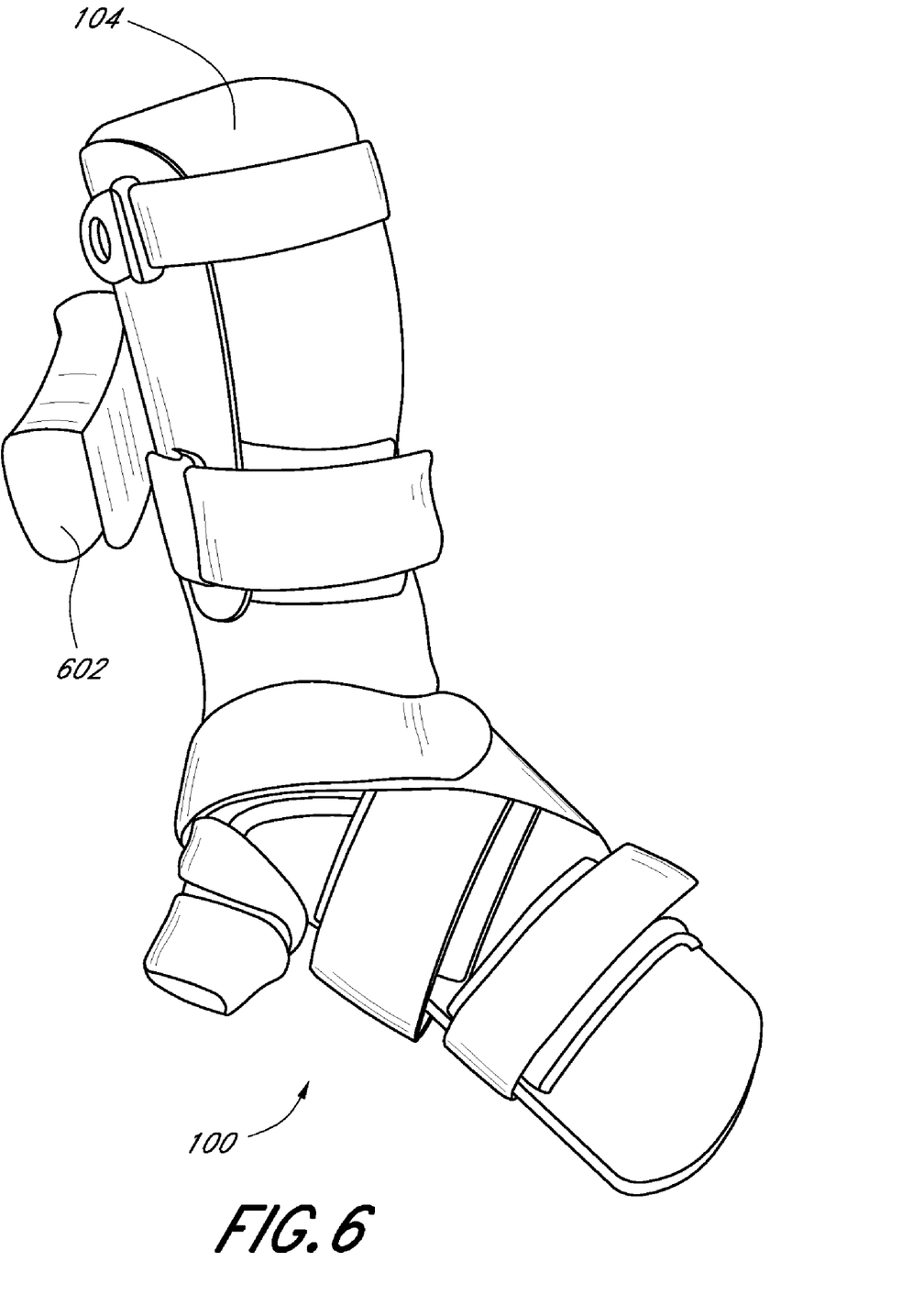
FIG. 6 illustrates generally the manner in which a patient's hand is positioned in the orthotic device of one embodiment of the present invention and the manner in which the device can be used to stretch the flexor tendon of the patient.

FIG. 6 shows another embodiment of the orthotic device 100 which includes a shoulder support 602. As shown, the shoulder support 602 is a U-shaped device adapted to hook to or be attached to the pants waist line of the patient. The shoulder support reduces the weight the device places on the patient's shoulder and also improves proper alignment of the patient's arm when the device is applied.

Figure 7:
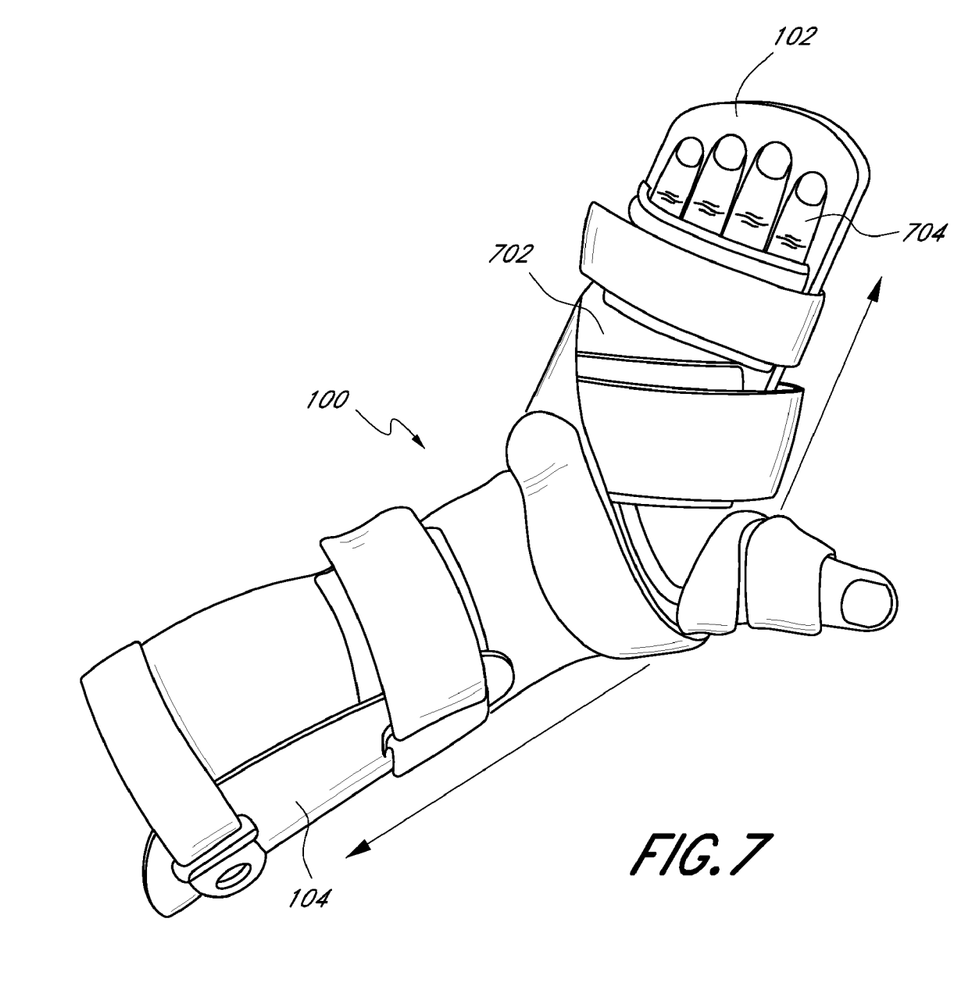
FIG. 7 illustrates a shoulder support used in conjunction with the orthotic device of certain preferred embodiments of the present invention.

As shown in FIG. 7, when the device 100 is applied to the patient's hand 702, the hand is supported by the hand support 102 and the forearm is positioned in and supported by the forearm support 104. The orthotic device 100 is designed to elongate the patient's flexor tendon and extend the range of movement by pivoting the hand support 104 upwardly in the manner as shown in FIG. 7. As also shown, the patient's fingers 704 are extended and wrist is not in flexion when the hand is positioned in the device 100. In one embodiment, the hand 702 is preferably positioned in a manner such that the fingers knuckles do not bend toward the palm of the hand. In this position, when the hand 702 is pivoted as shown in FIG. 7, the hand support exerts a force against the extended fingers 704, which help spread the metacarpal and elongate the flexor tendon and muscles that extend along the hand and the forearm. In another embodiment, the hand 702 is positioned in a manner such that the central arch region of the hand does not contact any part of the device and/or the device does not impart any pressure to the flexor tendon therein when the hand is moved during therapy. As shown and described, the device is configured to pivot the hand in a direction opposite the flexion direction so as to reverse the contractures. The degree of pivot can be progressively increased during therapy.

It will be appreciated that the concept of an orthotic device that is designed to extend the arches regions and to not apply pressure to the arch regions of an extremity or the flexor tendon therein in order to reduce spasms and hypertonicity is not limited to hand, wrist, or arm orthotic devices, but can also be applied to orthotic devices for treatment of other parts of the body, such as the foot and ankle, with the philosophy of promoting the opposite of what abnormality is observed.

Although the foregoing description of certain preferred embodiments of the present invention has shown, described and pointed out the fundamental novel features of the invention, it will be understood that various omissions, substitutions, and changes in the form of the detail of the device and methods as illustrated as well as the uses thereof, may be made by those skilled in the art, without departing from the spirit of the invention. Consequently, the scope of the present invention should not be limited to the foregoing discussions.

What is claimed is:

1. An orthotic device for reducing contracture and hypertonicity in patients with neurological disorders, comprising:
    a hand support, said hand support receives and positions a patient's hand in a manner such that the fingers of the hand are extended and the finger knuckles do not bend toward the palm of the hand, wherein the hand support comprises a palm rest portion and a thumb rest portion, said thumb rest portion is adapted to receive the patient's thumb and pivotable relative to the palm rest portion such that the angle therebetween can be adjusted;
    a forearm support that receives at least a portion of the patient's forearm, said forearm support is pivotably connected to the hand support; and
    attachment member that secures the device to the patient's hand and forearm.

2. The orthotic device of claim 1, wherein the hand support has a substantially planar interior surface, wherein the palm rest portion is located within said planar interior surface and said planar interior surface also comprises a fingers rest portion.

3. The orthotic device of claim 1, wherein said attachment member comprises a plurality of straps.

4. The orthotic device of claim 1, wherein said forearm support is pivotably connected to the hand support by a ratchet joint.

5. The orthotic device of claim 1, wherein said hand support has a plurality of padding, said padding is located in areas where the patient's digit fingers are to be positioned.

6. The orthotic device of claim 1, further comprising a shoulder support, said shoulder support reduces the weight the device places on the patient's shoulder, wherein said shoulder support comprises a U-shaped device adapted to be attached to the patient's pants waist line.

7. The orthotic device of claim 1, wherein the device further comprises an elbow support configured to receive and support the patient's elbow.

8. The orthotic device of claim 7, wherein the elbow support is connected to the forearm support via an interconnect member, wherein the interconnect member is configured to slidably engage with the forearm support so that the distance between the forearm support and the elbow support can be adjusted.

9. An orthotic device for reducing contracture and hypertonicity in patients, comprising:
    a hand support, said hand support including a palm rest portion, wherein said palm rest portion has a central portion and a peripheral portion surrounding said central portion; and wherein said central portion is not substantially higher than the peripheral portion;
    a forearm support that is connected to the hand support by a joint; and
    an elbow support that is connected to the forearm support, wherein the elbow support is slidably connected to the forearm support such that the distance between the elbow support and forearm support is adjustable, wherein said central portion is substantially below the peripheral portion so that the palm of the patient's hand receives force substantially entirely from the peripheral portion.

10. The device of claim 9, wherein said hand support further comprises a fingertip portion, wherein said fingertip portion is at substantially the same level as the peripheral portion of the palm rest portion so as to allow extensions of the patient's fingers without bending the finger knuckles.

* * * * *